US009987257B2

(12) United States Patent
Spector et al.

(10) Patent No.: US 9,987,257 B2
(45) Date of Patent: Jun. 5, 2018

(54) PEDIATRIC ORAL SUSPENSION FORMULATIONS OF AMOXICILLIN AND CLAVULANATE POTASSIUM AND METHOD FOR USING SAME

(71) Applicants: Michael Spector, Shamong, NJ (US); Alejandro Hoberman, Wexford, PA (US)

(72) Inventors: Michael Spector, Shamong, NJ (US); Alejandro Hoberman, Wexford, PA (US)

(*) Notice: Subject to any disclaimer, the term of this patent is extended or adjusted under 35 U.S.C. 154(b) by 0 days. days.

(21) Appl. No.: 14/371,731

(22) PCT Filed: Jan. 10, 2013

(86) PCT No.: PCT/US2013/021072
§ 371 (c)(1),
(2) Date: Jul. 10, 2014

(87) PCT Pub. No.: WO2013/106601
PCT Pub. Date: Jul. 18, 2013

(65) Prior Publication Data
US 2016/0339002 A1    Nov. 24, 2016

Related U.S. Application Data

(60) Provisional application No. 61/585,234, filed on Jan. 10, 2012.

(51) Int. Cl.
*A61K 31/43* (2006.01)
*A61K 31/424* (2006.01)
*A61K 9/10* (2006.01)
*A61K 9/00* (2006.01)
*A61K 9/16* (2006.01)

(52) U.S. Cl.
CPC ............ *A61K 31/43* (2013.01); *A61K 9/0095* (2013.01); *A61K 9/10* (2013.01); *A61K 31/424* (2013.01); *A61K 9/1617* (2013.01); *A61K 9/1623* (2013.01); *A61K 9/1652* (2013.01); *A61K 9/1688* (2013.01)

(58) Field of Classification Search
CPC .............................. A61K 31/43; A61K 31/424
See application file for complete search history.

(56) References Cited

U.S. PATENT DOCUMENTS

2005/0136117 A1    6/2005  Ramsey et al.
2006/0121106 A1*   6/2006  Kerc .................... A61K 9/0065
                                                                     424/451

FOREIGN PATENT DOCUMENTS

WO    WO 2006093784    *  9/2006  ........... A61K 31/635

OTHER PUBLICATIONS

Hoberman et al. (Pediatric Infectious Disease Journal: 1997, vol. 16, p. 463-470).*
Navarro et al. (Clin Pharmacokinet 2005; 44 (11): 1097-1115).*
Gordon ("Amoxicillin-Clavulanic Acid", Ch. 14 in Kucer's The Use of Antibiotics 6th ed (2010), p. 197-203).*
Bartlett JG. N Engl J Med 2002;346:334.*
Le (Rx Consultant, Feb. 2008, p. 1-8).*
Cooper CE, Slocombe B, White AR; Effect of Low Concentrations of Clavulanic Acid on the In-Vitro Activity of Amoxycillin Against Beta-Lactamase-Producing Branhamella Catarrhalis and Haemophilus Influenzae; J Antimicrob Chemother 1990; 26:371-80; Oxford University Press on behalf of the British Society for Antimicrobial Chemotherapy.
Nelson JD, Kusmiesz H, Shelton S.; Pharmacokinetics of Potassium Clavulanate in Combination with Amoxicillin in Pediatric Patients; Antimicrobial Agents and Chemotherapy 1982; American Society for Microbiology.
Hoberman A, Paradise JL, Rockette HE, et al.; Treatment of Acute Otitis Media in Children Under 2 years of Sge; N Engl J Med 2011; 364:105-15; Massachusetts Medical Society.
Tahtinen PA, Laine MK, Huovinen P, Jalava J, Ruuskanen O, Ruohola A;. A Placebo-Controlled Trial of Antimicrobial Treatment for Acute Otitis Media; N Engl J Med 2011; 364:116-26; Massachusetts Medical Society.
Hoberman A, Paradise JL, Rockette HE, et al.; Shortened Antimicrobial Treatment for Acute Otitis Media in Young Children; N Engl J Med 2016; 375:2446-56; Massachusetts Medical Society.

* cited by examiner

*Primary Examiner* — Robert Havlin
(74) *Attorney, Agent, or Firm* — Law Office of Theresa O'Rourke Nugent

(57) ABSTRACT

The invention is directed to a pediatric oral suspension composition containing amoxicillin and clavulanate potassium where the clavulanate potassium is present in an amount equal to or less than about 21.5 mg/5 mL, and a method of treating bacterial infections by providing between about one to about fourteen dosage days of the composition.

22 Claims, No Drawings

PEDIATRIC ORAL SUSPENSION FORMULATIONS OF AMOXICILLIN AND CLAVULANATE POTASSIUM AND METHOD FOR USING SAME

RELATED APPLICATIONS

This application claims priority from provisional application Ser. No. 61/585,234 filed Jan. 10, 2012 and PCT application PCT/US2013/021072.

FIELD OF THE INVENTION

The invention is for a pediatric oral suspension composition comprised of amoxicillin and clavulanate potassium.

BACKGROUND OF THE INVENTION

For pediatric administration of supplements and pharmaceuticals it is well recognized by those of skill in the art that solutions or liquid suspensions are highly preferable dosage forms. Tablets and capsules are difficult for children to swallow and the amount of drug delivered is not as flexible as is often required for pediatric drugs. With liquid dosage forms, by contrast, the amount of drug delivered to the patient can be varied over a wide range merely by regulating the volume of dose of known concentrations.

From the perspectives of ease of use, accuracy of dose, and bioavailability, oral liquid dosage forms are generally preferred to be in the form of a solution. From the perspective of taste, oral liquid dosage forms are generally preferred to be in the form of a suspension which tends to mask the taste of the drug. This is essentially useful with pediatric treatments as children generally do not like the taste of medicines. If the taste is not pleasing, the child can spit it out and therefore affect the treatment regimen. Especially for pediatric use, where doses are relatively small, accuracy and precision of dose is extremely important. For this reason, the preferable oral liquid form for many antibiotics for children is an oral suspension.

Amoxicillin is well known as a treatment for various bacterial infections and its use as an antibiotic, alone or in combination with other compositions and medications has been documented. However, treatment of certain bacterial infections has been made more difficult by resistance. In particular, many gram negative bacteria produce an enzyme, β-lactamase, that attacks the β-lactam ring of β-lactam antibiotics and renders them ineffective. To counteract this effect, β-lactamase inhibitors have been developed that can bind to β-lactamase and prevent it from attacking the antibiotic. The antibiotic and the inhibitor are preferably administered together. For example the β-lactam antibiotic amoxicillin can be administered with the β-lactamase inhibitor clavulanate potassium. This additional clavulanate potassium is not needed in non-beta lactamase mediated resistance treatments.

Moreover, the amount of amoxicillin has increased in dosage as certain bacteria have become resistant to the amoxicillin. For instance, *Streptococcus pneumoniae* have become resistant to amoxicillin such that the prescribed treatment dosage has increased from 400 mg/5 mL per day to over 600 mg/5 mL per day over the last decade. The amount of the clavulanate potassium has similarly increased or remained constant and in ratio with the increased amount of amoxicillin per dosage. Further the actual combined taken dosage for the patient, of the combined amoxicillin and clavulanate potassium has in fact doubled over the last few years, such as taking the dosage 2 or 3 times per day during treatment.

A combination of amoxicillin and clavulanate potassium is a treatment of choice for acute otitis media. Symptoms of acute otitis media include fever, otalgia, irritability and/or pain, fussiness, tugging or rubbing or holding of the ears, sleeping and feeding disturbances, and infrequently, perforation of the tympanic membrane. Most of these symptoms are mild to moderate and will eventually resolve spontaneously. The combination of amoxicillin and clavulanate potassium is considered the gold standard for antibiotic treatment, against which most new products on the market are compared. Resistant otitis media is on the rise in the pediatric population, it is believed, due to resistant organisms.

Acute otitis media remains the most frequently occurring infection for which antimicrobial agents are prescribed for children in the United States. Concerns about the development of antimicrobial resistance have led to recommendations to withhold antibiotics from such children unless symptoms persist or worsen, which is sometimes referred to as a "watchful waiting strategy", which can prolong the acute otitis media symptoms for the child.

Notably, due to vaccination there has been a selective reduction of treatable *S. pneumoniae* compared to resistant *Haemophilus influenzae* as causative agents. The resistance building up to amoxicillin has led to the increase of the dosage and/or dosage unit of amoxicillin in certain antibiotic compositions. Correspondingly, the other active pharmaceutical ingredients in such antibiotic compositions has also increased, typically based on ratios. Further, in addition to *H. influenzae*, another beta-lactamase bacteria of *Moraxella catarrhalis* is also seen in otitis media, although to a much lesser extent than *H. influenzae*.

Formulations of amoxicillin-clavulanate potassium have used varying ratios of the two components; over time, the trend has been to increase the dosage of amoxicillin, mainly to achieve higher efficacy rates against *S. pneumoniae*. Amoxicillin-clavulanate potassium ratios have thus ranged from 4:1 to 14:1. The currently available commercial amoxicillin-clavulanate potassium suspension for pediatric use contains 600 mg of amoxicillin and 42.9 mg of clavulanate potassium per 5 mL (a ratio of 14:1). The currently recommended pediatric dosage, 90/6.4 mg/kg/day administered in two divided doses for 10 days, results in a dose of clavulanate potassium almost twice as high as the dose recommended for adults (6.4 mg/kg/day vs. 3.5 mg/kg/day). The currently recommended adult dosage ranges from 500 mg/250 mg-4,000 mg/250 mg per day with a common dose being 1700 mg/250 mg per day.

Certain current formulations of amoxicillin and clavulanate potassium have a high concentration of clavulanate potassium. However clavulanate potassium has the potential to cause rare serious side effects such as jaundice and hepatitis (see, for example, Joint Formulary Committee. British National Formulary, 47th edition. London: British Medical Association and Royal Pharmaceutical Society of Great Britain; 2004). Other minor systemic reactions include headache, rash, mycosis, vaginitis, and agitation. The following infrequent and rare adverse reactions have been reported for ampicillin-class antibiotics: hepatitis; cholestatic jaundice; hemorrhagic/pseudomembranous colitis; angioedema; Stevens-Johnson syndrome; hypersensitivity vasculitis; tooth discoloration; and seizure.

More frequently, in pediatric patients clavulanate potassium may cause diarrhea (Reed, M. D. (1998) Clinical pharmacokinetics of amoxicillin and clavulanate potassium. Pediatric Infectious Disease Journal 17, 957-62), which can lead to dehydration in such young patients and further sickness. Although advantageous from the standpoint of efficacy, use of amoxicillin and clavulanate potassium is also associated with a relatively high incidence of diarrhea. This diarrhea is infrequently severe enough to require discontinuing treatment, but it may occasion delays in children's returning to day care and in parents' returning to work. While not being bound by theory, it is possible that the occurrence of diarrhea is related to the clavulanate potassium component of the drug combination.

Clavulanate potassium may also cause vomiting and diaper rash in children. These more common side effects of diarrhea, diaper rash, vomiting and oral moniliasis, while not as serious as the other side effects, are debilitating to the care givers of the pediatric patient. The pediatric patient with diarrhea and/or vomiting cannot return to school or day care until typically twenty-four (24) hours after the last episode of diarrhea or vomiting. Such constraints affect the parents and care giver of the pediatric patient in that they typically must use vacation days to stay home with the vomiting child, or work from home with a reduced productive outcome. Given the data that approximately twenty percent (20%) of all pediatric patients taking the current dosage of amoxicillin and clavulanate potassium experience some diarrhea and/or vomiting, this translates to twenty percent (20%) of children not able to return to school or day care and consequently twenty percent (20%) of parents or care givers staying home with the affected pediatric patient. It is thus discovered and sought to minimize the amount of clavulanate potassium necessary for treatment of children to be very useful.

While not wishing to be bound by theory, it is possible that clavulanate potassium has the property of binding irreversibly to β-lactamase. (Reed, M. D. (1998). Clinical pharmacokinetics of amoxicillin and clavulanate potassium. Pediatric Infectious Disease Journal 17, 957-62), thus enhancing the effectiveness of amoxicillin. If so, then this might explain the rapidly declining need for clavulanate potassium in the course of a combined treatment with amoxicillin and clavulanate potassium. After an initial loading dose of clavulanate potassium is provided, either the same amount or much less may be needed. Continuing to administer the same composition of amoxicillin and clavulanate potassium over the treatment regimen period, as the currently prescribed method, may result in too much clavulanate potassium being taken in subsequent doses.

Clearly for a pediatric population it is particularly important to use the minimal, yet effective, amount of clavulanate potassium so as to reduce the risk of diarrhea, diaper dermatitis and vomiting in a young population. We have discovered that overall less clavulanate potassium is required for the entire treatment regimen, which can either be (a) a lower dose through the regimen, (b) high dose of clavulanate potassium at the beginning of treatment to bind to β-lactamase and then less throughout the regimen, or (c) a combination thereof and varying dosages throughout the treatment regimen. Thus, either the same smaller amount, or less, clavulanate potassium may be required as treatment progresses. However in current treatments amoxicillin and clavulanate potassium are administered in a set combined dosage form administered at the same level at a ratio of about 4:1-14:1 over a period of days (typically ten (10) days). Although various amoxicillin and clavulanate potassium regimens are available, the need for minimizing clavulanate potassium has not been adequately addressed. Until recently, the thrust behind reformulations of amoxicillin-clavulanate potassium has been adequate coverage of *S. pneumoniae*. Currently, focus has shifted to adequate coverage of *H. influenzae*. However, minimizing adverse events and side effects has not been given precedence over the efficacy of the dosage formulation to address *S. pneumoniae, H. influenzae* and other causes of infections.

For instance, in a study published in the New England Journal of Medicine in January 2011, the table below (Table 1) shows the higher rates of diarrhea, vomiting and diaper dermatitis in children taking amoxicillin-clavulanate potassium versus those taking a placebo.

TABLE 3

Complications and Adverse Events According to Study Group and Treatment Received at the Time of Occurrence.*

| Adverse Event | Amoxicillin-Clavulanate Group (N = 144) | | | Placebo Group (N = 147) | | |
| --- | --- | --- | --- | --- | --- | --- |
| | During Receipt of Amoxicillin-Clavulanate | During Receipt of Rescue Therapy | Total | During Receipt of Placebo | During Receipt of Rescue Therapy | Total |
| | number of children (percent) | | | | | |
| Mastoiditis† | 0 | 0 | 0 | 1 (1) | 0 | 1 (1) |
| Perforation of tympanic membrane | 1 (1) | 0 | 1 (1) | 6 (4) | 1 (1) | 7 (5) |
| Protocol-defined diarrhea‡ | 34 (24) | 2 (1) | 36 (25) | 11 (7) | 11 (7) | 22 (15)§ |
| Diaper-area dermatitis | 67 (47) | 6 (4) | 73 (51) | 24 (16) | 27 (18) | 51 (35)¶ |
| Oral thrush | 7 (5) | 0 | 7 (5) | 0 | 1 (1) | 1 (1) |
| Vomiting‖ | 12 (8) | 0 | 12 (8) | 11 (7) | 1 (1) | 12 (8) |
| Rash** | 1 (1) | 0 | 1 (1) | 1 (1) | 1 (1) | 2 (1) |

*In each study group, one child was not followed beyond enrollment. Comparisons were adjusted for study site, history or no history of recurrent acute otitis media, and exposure or no exposure to other children.
†Mastoiditis developed on day 5 in an 11-month-old child with unilateral acute otitis media and a score on the Acute Otitis Media Severity of Symptoms (AOM-SOS) scale of 14 at entry and of 7 on day 5. A culture of middle-ear aspirate yielded serotype 19A *Streptococcus pneumoniae* with a penicillin minimum inhibitory concentration of 2 μg per milliliter. The child was hospitalized for 41 hours and treated initially with parenteral antibiotics and subsequently with oral antibiotics; he recovered uneventfully.
‡Diarrhea was defined in the protocol as three or more watery stools in 1 day or two watery stools daily for at least 2 days. Treatment was discontinued because of diarrhea in six children in the amoxicillin-clavulanate group and one child in the placebo group, in whom *Clostridium difficile* enteritis developed.
§P = 0.05 for the difference between the amoxicillin-clavulanate group and the placebo group.
¶P = 0.008 for the difference between the amoxicillin-clavulanate group and the placebo group.
‖In the amoxicillin-clavulanate group, treatment was discontinued in one child because of vomiting.
**In each group, treatment was discontinued in one child because or rash.

Thus, a need exists for an amoxicillin-clavulanate potassium composition, and treatment method, which reduces the side effects of diarrhea, vomiting and diaper dermatitis in children, while still maintaining the high efficacy of the antibiotic combination. One of the objectives of the invention is to maintain high efficacy while improving safety profile, namely reducing the common and disruptive side effects of diarrhea, vomiting and diaper dermatitis in pediatric patients.

Various formulations and dosing modalities currently exist for the combination of amoxicillin-clavulanate potassium. Tablets and suspensions are also available. Delayed release tablet formulations have been developed (see for example U.S. Pat. Nos. 5,910,322; 6,299,903; 6,544,558; 6,756,057; 6,783,773; 6,977,086; 7,122,204; 7,534,781; and publications 2006/0121106, 2008/0300569, and 2011/0020408).

However, these systems provide combination doses of amoxicillin-clavulanate potassium that do not address the need for a reduced set amount of clavulanate potassium (whether constant throughout the treatment or in a reduced set amount when compared to current conventional and known amounts) throughout the treatment regimen, including reducing the amount as treatment progresses. There is a need for a dosage, and a method that provides a means of reducing the overall amount of clavulanate potassium for the treatment regimen, when compared to current conventional and known dosage amounts and methods of treatment.

Thus, a need exists for a pediatric oral suspension composition having amoxicillin-clavulanate potassium to maintain the efficacy of the composition in view of beta-lactamase mediated resistance *H. influenzae* and *M. catarrhalis*, without elevating the possibility of the severe side affects of jaundice and hepatitis and the more common and disruptive side effects of diarrhea, diaper rash and vomiting.

These and other needs are met by the present invention including a composition and a method for treating bacterial infections, including acute otitis media and other respiratory infections such as but not limited to acute bacterial rhinosinusitis. Other advantages of the present invention will become apparent from the following description and appended claims.

SUMMARY OF THE INVENTION

This invention provides an oral suspension composition for pediatric use including an amount of amoxicillin and an amount no greater than 21.5 mg/5 mL of clavulanate potassium.

Also part of this invention is a method of treatment for acute otitis media in pediatric patients including multiple days of dosage of a composition of amoxicillin and clavulanate potassium, with the clavulanate potassium present in an amount no greater than 21.5 mg/5 mL, and a method including multiple days of dosage, where the clavulanate potassium amount is constant or reduced over the dosage days. This invention includes methods for treating conditions such as acute otitis media in children.

Also part of this invention is an oral suspension composition for pediatric use including an amount of amoxicillin and an amount of clavulanate potassium in at a ratio of at least 28:1, preferably in a range of 28:1 through 56:1.

DETAILED DESCRIPTION OF THE INVENTION

The invention includes a pediatric oral suspension composition for treating acute otitis media comprised of amoxicillin and clavulanate potassium where the amount of clavulanate potassium is less than 21.5 mg/5 mL. A multiple day dosage method is included.

Another embodiment of the invention is a pediatric oral suspension composition for treating acute otitis media comprised of amoxicillin and clavulanate potassium in a ratio of at least 28:1. A multiple day dosage method is included.

For purposes of this invention, the following terms have the meanings given below unless otherwise indicated.

"Unit Dose" means a discrete dose of a composition of this invention given once, in a single administration.

"Dose" or "dosage" may mean either a single administration of a composition or can mean several administrations of the same composition depending on context. For example if the composition is given twice a day, a dose could be taken to mean two administrations of the same composition, in suitably measured amounts. Thus the same "dose" may be given two or three times (or more if necessary) in the treatment regimen before progressing to the subsequent dose, which would be of a composition having a different given amount of medication. However as defined above a unit dose means a single dose given a single time, i.e. in one administration.

"Dosage form" is the type of formulation in which the compositions of this invention are administered, such as but not limited to amoxicillin-clavulanate potassium. A dosage form may be a discrete unit such as a tablet or may be a liquid form or a suspension, from which unit dosages are measured.

"Patient" may be any living thing treated with a composition of this invention. The patient is preferably a human child, but could also be an adult or non-human such as an animal.

"About" when used in connection with an amount shall mean a scientifically reasonable variance above and below that amount keeping in mind artifacts of measurement and other variables. For example, a ratio of about 1:15 may encompass ±5% of the unit of measure used. A concentration of 1 mg/mL may encompass a range of about ±0.05 mg, while a concentration of 1000 mg/mL may encompass a range of ±50 mg.

"Amoxicillin" and "clavulanate potassium" or "clavulanic acid" refer to any existing acid and salt forms, whether alkali, alkaline, or acid salts, polymorphs, hydrates, solvates, racemates and mixtures. Examples are amoxicillin trihydrate or sodium, and potassium clavulanate. The weights of amoxicillin and clavulanate potassium refer to weight in equivalents of corresponding free acids unless otherwise indicated. The weights used in a formulation may also be adjusted by known methods depending on potency.

Standard abbreviations may be used. All publications cited herein, including but not limited to patents and patent applications, are incorporated by reference in their entirety as if individually specified as incorporated by reference, unless otherwise indicated.

The inventive composition includes amoxicillin and clavulanate potassium. Clavulanate potassium includes clavulanic acid, which is the generic name for (2R,5R,Z)-3-(2-hydroxyethylidene)-7-oxo-4-oxa-1-azabicyclo[3.2.0]heptane-2-carboxylic acid, which is a known compound of the following formula:

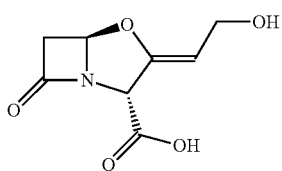 [SMILES: O=C(O)[C@H]1/C(=C/CO)O[C@@H]2CC(=O)N21]

The inventive composition also includes amoxicillin, which is an analog of ampicillin, derived from the basic penicillin nucleus 6-aminopenicillanic acid. Chemically, a=Amoxicillin is (2S,5R,6R)-6-[I-(−)-2-amino-2-(p-hydroxyphenyl)acetamido]-3,3-dimet-7-oxo-4-thia-1-azabicyclo[3.2.0]heptane-2-carboxylic acid.

The composition of the invention contains no more than 21.5 mg/5 mL of clavulanate potassium, with amoxicillin within the inventive composition. Preferably the clavulanate potassium is present in an amount of between about 5 mg/5 mL to about 21.5 mg/5 mL.

A particularly preferred mode of administration for use with children is orally via an aqueous suspension. For preparing such suspensions amoxicillin and clavulanate potassium can be combined with buffers, emulsifying and suspending agents. If desired, certain sweetening and/or flavoring agents can be added. These active compounds can be directly mixed with liquid ingredients to provide a suspension, or can be formed into granules or powders which are then made into a suspension, by known methods and using known ingredients examples of which are provided below. The resulting suspension can be stored in the presence of water, especially if refrigerated, for an appropriate period. However, a preferred method is to store the mixture as a dry powder until its use is required, at which time it is mixed with an appropriate diluent, e.g., water.

The prescribing physician will ultimately determine the appropriate dose for a given human pediatric subject, and this can be expected to vary according to the age, weight, and response of the individual pediatric patient as well as the nature and severity of the patient's symptoms. The compounds of this invention will normally be used orally at dosages in the range from about 3.2 mg/kg/day for children weighing less than 40 kg. In some instances it may be necessary to use doses outside these ranges.

Dosage forms contemplated for the compositions of this invention containing amoxicillin and clavulanate potassium, include any known liquids for pharmaceutical use, preferably oral suspensions as the typical patient will be a human child. The most common formulation is a powder for suspension to be mixed with water at the time of use.

The inventive composition may also contain excipients, vehicles, and solvents include sterile water, saline, Ringer's solution, polyalkylene glycols, natural and synthetic fatty acids, mono, di, and triglycerides and oils, and hydrogenated naphthalenes. Carriers may be included such as but not limited to lactose, saccharose, sorbitol, mannitol, starch, amylopectin, cellulose derivatives, and gelatin.

Disintegrants may be included such as but not limited to starch such as pregelatinized and sodium starch glycolate, cellulose such as microcrystalline, sodium carboxymethyl, hydroxypropyl, croscarmellose sodium, crosspovidone, and crosslinked polyvinyl pyrrolidone. Fillers may be included such as but not limited to cellulose, dibasic calcium phosphate, lactose, sucrose, glucose, mannitol, sorbitol, calcium carbonate, and fats and oils for capsules.

Antifriction agents may be included such as but not limited to magnesium and calcium stearates, and polyethylene glycol waxes. Glidants may be included such as but not limited to colloidal silicon dioxide and talc. Lubricants may be included such as but not limited to talc, silica, colloidal silicon dioxide, and fats such as zinc or magnesium stearate or stearic acid. Preservatives may be included such as but not limited to e m-cresol, p-cresol, o-cresol, chlorocresol, benzyl alcohol, phenylmercuric nitrite, phenoxyethanol, formaldehyde, chlorobutanol, magnesium chloride (hexahydrate), benzalkonium chloride, benzethonium chloride, sodium dehydroacetate, thimerosal, antioxidants (vitamins A, C, E, retinyl palmitate), selenium, cysteine, methionine, citric acid, sodium citrate, and lower alkylparabens. Mucoadhesives may be included such as but not limited to methyl, hydroxypropyl, and sodium carboxymethyl cellulose, chitosan, polyvinyl pyrrolidone, and hydrogels.

Binders may be included such as but not limited to polyvinylpyrrolidone, pregelatinized starch, methacrylic acid polymers, gelatin, and hydroxypropylcellulose. pH modifiers may be included such as but not limited to various organic and inorganic acids, bases, and their salts such as orthophosphoric acid, hydrochloric acid, nitric acid, sulphuric acid, sulfamic acid, hydrofluoric acid, oxoacids, sodium and potassium dihydrogen phosphates, citric acid, ascorbic acid, tartaric acid, malic acid, malonic acid, succinic acid, fumaric acid, maleic acid, adipic acid, lactic acid, levulinic acid, sorbic acid, polyacrylic acid, sodium carbonate, sodium bicarbonate, magnesium carbonate, magnesium oxide, calcium carbonate, calcium oxide, aluminum hydroxide, magnesium hydroxide, and sodium hydroxide.

Buffers may be included such as but not limited to acetic acid, citric acid, boric acid, and phosphoric acid. Isotonicity agents may be included such as but not limited to glycerin, mannitol, sorbitol, sodium chloride, and other electrolytes. Emulsifiers may be included such as but not limited to soy lecithin, calcium stearoyl dilactate, various esters of polyglycerol and sorbitan, and monoglycerides. Suspending agents may be included such as but not limited to natural and synthetic polysaccharides such as gums (acacia, tragacanth, guar, and xanthan), celluloses (sodium carboxymethyl, methyl, hydroxyethyl, hydroxypropyl, and microcrystalline), carageenan, sodium alginate, carbomer, colloidal silicon dioxide, and clays (aluminum magnesium silicate, bentonite, hectorite).

Further components such as solubilizers may be added including but not limited to Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) and non-ionic surfactants such as polysorbate 20 or 80 or poloxamer 184 or 188, polyols, other block co-polymers, and chelators such as EDTA and EGTA.

Flavorants may be included such as but not limited to sodium saccharin, sugar, and other natural and artificial compounds which mask or enhance flavor. Colorants may be included such as but not limited to natural dyes such as caramel coloring, annatto, cochineal, betanin, turmeric, saffron, paprika, elderberry, pandan, and butterfly pea, and artificial dyes such as FD&C Blue Nos. 1 and 2, Green No. 3, Yellow Nos. 5 and 6, and Red Nos. 3 and 40. Thickening agents may be included such as but not limited to alginic acid and salts (such as sodium, potassium, ammonium, calcium), agar, carrageenan, locust bean gum, gelatin, and pectin. Stabilizing agents may be included such as but not limited to fatty acid salts, sulfates, sulfate esters and phosphate esters (for example polyoxyethylene fatty acid esters and alcohols, and polyoxyethylene sorbitol fatty acid esters such as polyoxyethylene sorbitan monooleate, polysorbate 80 and polysorbate 20). Surfactants may be included such as but not limited to sorbitan trioleate, soya lecithin, and oleic acid.

The sweetener of the composition may be any natural or synthetic compound, or combination of compounds, which provides adequate sweetening to overcome the bitterness of the inventive composition. Natural sweeteners include carbohydrates such as sucrose, dextrose, fructose, invert sugar, mannitol, sorbitol, and the like. Synthetic sweeteners include saccharin, aspartame, cyclamates, and other so-called artificial sweeteners familiar to those of skill in the art. The flavoring of the composition may be any natural or synthetic compound, or combination of compounds, which provides acceptable taste to overcome the blandness of the base composition. Such flavorings include bubble gum, grape, cherry, berry, citrus, other fruits, peppermint, spearmint, other mints, vanilla, chocolate, and the like, familiar to those of skill in the art.

In more detail, the compositions of this invention may be liquid formulations for oral use. Such formulations may include a suitable selection of appropriate known ingredients such as those provided above alone or in combination. The liquid formulations may be formulated as syrups, solutions or emulsion, elixir, suspensions or other known types of liquid suitable for oral administration. The liquid formulations may be aqueous or nonaqueous and include for example buffers with any pharmaceutically acceptable salts, preservatives, emulsifiers, humidifiers, isotonicity agents, solubilizers, buffers, thickening and suspending agents, dyes, and flavorants.

Specific ingredients may include water, saline, polyalkylene glycols, oils, hydrogenated naphthalenes, sugar, ethanol, glycerol, propylene glycol, dyes, flavorants, and thickening agents. The liquid formulations may be prepared by known methods using the compositions of this invention. The active compounds of the amoxicillin and clavulanate potassium may be obtained from existing powders, granules, or tablets for liquid formulations.

The liquid formulations of this invention may be provided for oral administration. For example the formulations may be taken in measured doses using a cup, straw, spoon, syringe, or other device. The formulations may be provided in liquid form, or may be provided in dry form (for example granule or powder) to which an appropriately formulated water or liquid solvent is added to provide a liquid formulation of a composition of this invention. Ingredients suitable for liquid formulations are known and such a formulation may be made by methods known in the art.

A liquid formulation (for example solution, suspension, emulsion) can be made by combining the amoxicillin and clavulanate potassium with suitable aqueous and or nonaqueous diluents, water, buffers, and preservatives as discussed above and mixing with known methods under suitable known conditions. The specific ingredients and concentrations will depend on the type of formulation desired, for example oral suspension as known in the art. However, as an example, a pediatric oral suspension may also include a vehicle such as water, saline, Ringer's solution, dextrose, serum albumin, sodium chloride, mannitol, buffers, and preservatives. The formulation may be sterilized by known techniques.

Certain known dosing combinations of amoxicillin and clavulanate potassium are listed in Table 2 below. In these conventional dosing combinations the amount of clavulanate potassium is between about 28.5 mg/5 mL to about 62.5 mg/5 mL. The previous known and used ratios of amoxicillin to clavulanate potassium are between 4:1 to 14:1.

TABLE 2

|   | Amoxicillin | Clavulanate potassium | Ratio |
|---|---|---|---|
| 1 | 125 mg/5 mL | 31.25 | 4:1 |
| 2 | 200 mg/5 mL | 28.5 | 7:1 |
| 3 | 250 mg/5 mL | 62.5 | 4:1 |
| 4 | 400 mg/5 mL | 57 | 7:1 |
| 5 | 600 mg/5 mL | 42.9 | 14:1 |

The inventive composition instead contains amoxicillin and clavulanate potassium wherein the amount of clavulanate potassium does not exceed 21.5 mg/5 mL. Further, another embodiment of the inventive composition contains amoxicillin and clavulanate potassium in a ratio of at least 28:1 and preferably between 28:1 and 56:1. Both embodiments of the invention result in a reduced amount of clavulanate potassium compared to current known compositions. While not being bound by theory, the reduced amount of clavulanate potassium may be especially good for pediatric patients as it may lead to reduced chance of diarrhea, vomiting, and diaper rash in such patients. The reduced amount of clavulanate potassium does not affect the treatment efficacy of the amoxicillin to treat acute otitis media or other illnesses such as respiratory illnesses.

The method of the invention is to treat pediatric patients with a dosing regimen of about one to about fourteen days, using a composition of amoxicillin and clavulanate potassium wherein the clavulanate potassium is present in an amount not to exceed 21.5 mg/5 mL. In one embodiment of the method of the present invention the amount of clavulanate potassium remains constant, with the amount being less than 21.5 mg/5 mL.

In another embodiment of the method of the present invention it is preferred that the first dose contains more of clavulanate potassium, than the second, or any subsequent dosage. For example, in a multiple day method spanning ten (10) days, the dosage of clavulanate potassium on days 1 and 2 may be in an amount of 21.5 mg/5 mL, then an amount of 15 mg/5 mL on days 3-10.

A further embodiment of the method of the present invention includes a dosage for the first two days of the treatment containing no more than 21.5 mg/5 mL of clavulanate potassium and then the subsequent dosages contain a less amount of clavulanate potassium. In yet another embodiment of the method of the present invention the first dose contains more of the clavulanate potassium than the second dose, and the subsequent dosages contain decreasing amounts of clavulanate potassium. The less amount of clavulanate potassium may be constant or can continue to decrease over the treatment days. For example, in a multiple day method spanning ten (10) days, the dosage of clavulanate potassium on days 1 and 2 may be in an amount of 21.5 mg/5 mL, then an amount of about 15-20 mg/5 mL on days 3-6, and an amount of about 5-10 mg/5 mL on days 7-10. In all the embodiments of the inventive method the amounts used should be effective for the treatment contemplated, as can be determined by a person skilled in the art.

In another embodiment of the inventive method, the method of the invention is to treat pediatric patients with a dosing regimen of one to about fourteen days, using a composition of amoxicillin and clavulanate potassium in a ratio of at least 28:1. In another embodiment of the method of the present invention it is preferred that the first dose contains more of clavulanate potassium, than the second, and any subsequent dosages contain decreasing amounts of clavulanate potassium, so that the ratio increases over the dosage treatment regimen. The amounts used should be effective for the treatment contemplated, as can be determined by a person skilled in the art.

The amounts of the amoxicillin in either embodiment of the inventive method, will preferably remain the same during the treatment regimen, but may also decrease, or may even increase for any treatment that would require increasing amounts. The amounts of the clavulanate potassium may decrease with each dosage or may remain constant over several doses, or even increase if the treatment requires. It is most preferable that the amount of the clavulanate potassium, decreases with successive dosages. The dosages may be formulated to contain more than one unit dose and thus be administered more than once. Thus it is possible that two or more successive dosages as administered may contain the same amount of the clavulanate potassium, while the next subsequent dosage contains less. The dosages may also be provided as a unit dose, in which case each is only provided once. Any combination of dosages and unit doses may be used. One embodiment of the method is for a multiple day dosage wherein the clavulanate potassium is a constant amount over the treatment days, with the days being anywhere from about two days to about fourteen days or more. Another embodiment of the method is for a multiple day dosage wherein the clavulanate potassium is reduced over the dosage period. The dosage period may also be about two days or increased up to about fourteen days or more, with either constant or reduced clavulanate potassium over the dosing period.

For instance, the amount or concentration of the clavulanate potassium can remain constant in the ratio of at least 28:1 to the amoxicillin, or could taper down in succeeding dosages of the method. In the reducing embodiment, thus each composition will contain less of the clavulanate potassium and the ratio will increase. The final dosing composition may optionally contain none of the clavulanate potassium.

In general the compositions of this invention contain effective amounts for the treatment contemplated of the amoxicillin and clavulanate potassium. These amounts may be determined by a skilled person with routine experimentation.

However, preferred amounts of amoxicillin and clavulanate potassium are provided as follows. In any liquid formulations of the compositions of this invention described above, preferably suspensions, each composition may contain from about 100 to about 1200 mg/5 mL (or about 20 to about 140 mg/mL) of amoxicillin and about 0.1 to about 21.5 mg/5 mL of clavulanate potassium. The compositions preferably contain from about 125 mg/6 mL to about 600 mg/5 mL of amoxicillin. Preferably the amount of clavulanate potassium is from about 0.01 mg/5 mL to about 21.5 mg/5 mL of liquid formulation. The amount of clavulanate potassium may be about 22.6 mg/5 mL. For purposes of dosing 5 mL is equal to one teaspoon.

For any given dispensing system of this invention, the amount of clavulanate potassium in the first composition should preferably determine the amount in the second (and succeeding) compositions in an embodiment wherein there will be the same or less clavulanate potassium in succeeding doses. For example, if the first composition contains 600 mg/5 mL of amoxicillin and 21.5 mg/5 mL of clavulanate potassium, then the second dosing composition contains equal to or less than 21.5 mg/5 mL clavulanate potassium.

This invention is also directed to a liquid composition of amoxicillin and clavulanate potassium which contains less than about 21.5 mg/5 mL and more than 0.1 mg/5 mL of clavulanate potassium. A preferred composition has from about 15 mg/5 mL to about 21.5 mg/5 mL. Another preferred composition has an amount of clavulanate potassium of about 22.6 mg/5 mL Another preferred composition has from about 10 mg/5 mL to less than 21.5 mg/5 mL. Another preferred range is from about 2.5 mg to about 10 mg of clavulanate potassium.

The concentrations of the invention are preferably expressed in mg as above. This invention also contemplates ratios to express the concentrations. For example the amoxicillin may be present in a ratio of about 28:1 to about 56:1 where 1 represents the amount of the clavulanate potassium. Preferably the amount of the amoxicillin is from about 30:1 to about 35:1. These ratios are preferably weight ratios. As discussed above, compositions of this invention may start with any amount or concentration of the clavulanate potassium as long as the succeeding compositions contain the same or lower amounts or concentrations.

The amounts and concentrations of the pharmaceutically active compounds, preferably amoxicillin and clavulanate potassium, may also be determined by known methods using desired serum concentrations at various points in the treatment regimen.

The compositions of the present invention can be prepared by known processes. Amoxicillin and clavulanate potassium, the preferred pharmaceutically active compounds can be obtained from suppliers or made by known methods. See for example U.S. Pat. Nos. 6,218,380 and 7,534,781.

The formulations discussed above can be made by methods known in the art using the various "inactive" formulation ingredients discussed with amoxicillin and clavulanate potassium. These known ingredients can be made by methods known in the art or obtained from chemical supply houses. The amounts and concentrations preferred for the amoxicillin and clavulanate potassium compositions of this invention are discussed above. The amounts of the other ingredients should be sufficient to provide the properties for which each of the ingredients are being used, for example, flavorant or other additives.

Liquid formulations of compositions of this invention can be prepared by mixing the pharmaceutically active compounds preferably amoxicillin and clavulanate potassium with a preservative and any desired buffers in an aqueous diluent using conventional procedures for mixing, suspension or dissolution. Liquid formulations can be made by reconstituting powders or granules or lyophilized preparations.

Suspensions of this invention may be provided at any concentration providing acceptable stability for the pharmaceutically active compounds (for example the length of the desired treatment period, optionally with refrigeration) and within the range that would provide a composition having suitable flow parameters for dispensing systems of this invention. Reconstituting oral suspensions from an amoxicillin and clavulanate potassium powder composition may be done as follows from a powder prepared for oral suspension. The suspension may be prepared from freely flowing powder in a suitable container. A little over half of the solvent such as water needed should be added and the container shaken vigorously to suspend. Then the rest of the solvent should be added and the container shaken vigorously.

The preferred active ingredients are amoxicillin and clavulanate potassium used together in the treatment regimen described, however other active ingredients may be used in the same type of composition of this invention. Further, the amoxicillin and clavulanate potassium may be present throughout the multiple day dosing method in a constant amount of about 21.5 mg/5 mL or less of clavulanate potassium to at least 600 mg/5 mL, or more of amoxicillin, in a ratio of at least about 28:1.

Any pharmaceutically acceptable formulation of the compositions of this invention including the amoxicillin and clavulanate potassium at a ratio of at least about 28:1 may be used in the dispensing systems of this invention. Such compositions may contain pharmaceutically acceptable ingredients whose nature and amounts will be known to a skilled practitioner depending on the dosage form and route of administration selected. Amoxicillin and clavulanate in any pharmaceutically acceptable form may be used in any combinations, including salts, complexes, prodrugs, hydrates, solvates, or polymorphs. Clavulanate potassium is preferred. Other pharmaceutically active ingredients may also be included in the compositions of this invention.

This invention is directed to a method of treatment by providing two or more doses of a composition containing amoxicillin and clavulanate potassium. A preferable condition to be treated is a bacterial infection, most preferably acute otitis media. Other conditions for treatment include respiratory bacteria illness such as sinusitis.

The patient or treatment subject may be a human, preferably a human child. Other patients may include non-humans such as animals. Therefore the method would include a veterinary method to treat infections, viruses and bacteria in mammals, fish, birds and animals.

The amount of the compounds used in the inventive composition and method of treatment are amounts effective to treat the condition. More specific amounts have been discussed in detail above. The dosage will depend on the age, weight, condition, and disease of the patient. In general the compositions of this invention contain effective amounts for the treatment contemplated of the amoxicillin and clavulanate potassium. These amounts may be determined by a skilled person with routine experimentation.

The method of the claimed invention may include two or more doses of amoxicillin combined with clavulanate potassium where the dosing remains constant or the initial doses contain more or less clavulanate potassium than any subsequent doses. The clavulanate potassium amount may be constant throughout the dosage, with the amount being less than conventional dosages, such as less than about 21.5 mg/5 mL. In another embodiment, the initial dose may be a unit dose which contains more clavulanate potassium than the second dose which is a unit dose and any subsequent unit doses. The initial dosage may be more than one unit dose containing more clavulanate potassium than the second and subsequent unit dosages which also may include more than one unit dose. Similarly the first dose may be a unit dose and subsequent dosages include more than one unit dose. The first dosage may be more than one dose and second and/or subsequent doses may be unit doses. The distinction between the first and subsequent doses is an embodiment of this invention.

In a further embodiment of the inventive method, the treatment regimen may be over multiple days where the initial dosage amount of clavulanate potassium is about or less than about 21.5 mg/5 mL, the middle doses are a higher amount than the first while still being less than about 21.5 mg/5 mL, and the next subsequent doses are in an amount lower than the middle doses. For example, in a multiple day method spanning ten (10) days, the dosage of clavulanate potassium on days 1 and 2 may be in an amount of about 10-19 mg/5 mL, then an amount of about 20-21.5 mg/5 mL on days 3-6, and an amount of about 5-10 mg/5 mL on days 7-10.

The compositions of this invention and the methods of this invention may be used to provide various treatment regimens to patients as methods of treatment of this invention. A method of treatment regimen of the present invention may be one day or multiple days, between about two days to about fourteen days, though it is preferred the dosing be for about three through about ten days. The dosage schedule below are given solely as examples, many others may readily be developed by a skilled practitioner based on known methods and information provided herein. In these examples "day" is a twelve hour period.

For example a treatment period of about ten days providing amoxicillin and clavulanate potassium wherein the dosing remains constant of amoxicillin and clavulanate potassium where the clavulanate is in an amount of about 21.5 mg/5 mL or less.

Another example of a treatment period of ten days may include the following dosing as follows:

Days 1-4: 600 mg/kg amoxicillin and 21.5 mg/kg clavulanate potassium; and

Days 5-10: 600 mg/kg amoxicillin and 10.75 mg/kg clavulanate potassium, should provide suitable dosages for a pediatric patient.

In another embodiment a treatment period of ten days providing amoxicillin and clavulanate potassium wherein the dosing remains constant of amoxicillin and clavulanate potassium where the clavulanate potassium is present in an amount of about 21.5 mg/5 mL or less.

Another example of a treatment period of ten days may include the following dosing as follows:

Days 1-2: 600 mg/kg amoxicillin and 21.5 mg/kg clavulanate potassium;

Days 3-5: 600 mg/kg amoxicillin and 10.75 mg/kg clavulanate potassium; and

Days 6-10: 600 mg/kg amoxicillin and 5.5 mg/kg clavulanate potassium, should provide suitable dosages for a pediatric patient.

As can be seen this exemplary regimen can be modified for different formulations, reduced or extended in length, and designed to provide further clavulanate potassium gradients if desired, by varying the amounts and concentrations of the compositions of this invention and selecting the appropriate dispensing system of this invention. Other examples will be apparent to a skilled practitioner and are part of this invention.

Preferably the amount of clavulanate potassium in subsequent dosages is from about 0.1 mg/5 mL of suspension to about 21.5 mg/5 mL of suspension. More preferably the amount of clavulanate potassium is from about 10 mg/5 mL of suspension to about 21.5 mg/5 mL of suspension.

In general, this invention provides methods of treatment as discussed above for infections in a patient, of any part of the body including specific cells, tissues, or organs. The infections may be acute or chronic and are primarily bacterial such as meningitis, peritonitis, *Chlamydia pneumoniae, S. pneumoniae, listeriosis, salmonellosis*, toxic shock syndrome, *tuberculosis*, and other bacterial infections. Syndromes and conditions caused by bacterial infections may also be treated, such as hemolytic uremic syndrome and Lyme disease.

Bacterial infections for treatment with the compositions of this infection include but are not limited to acute otitis media and other infections such as those of the lower respiratory tract, sinusitis, skin and skin structure infections and urinary tract infections. These can be caused by caused by various bacteria both gram positive and gram negative. Among them are *staphylococcus aureus, Enterobacter* species in urinary tract infections, *escherichia coli, H. influenzae, M. catarrhalis, S. pneumoniae, Neisseria gonorrhoeae, Eikenella corrodens, Proteus mirabilis, Enterococcus faecalis, Staphylococcus epidermidis, Staphylococcus saprophyticus, Streptococcus pyogenes, viridans* group *streptococcus, Klebsiella* species *Bacteroides* species, *Fusobacterium* species, and *Peptostreptococcus* species.

As discussed above there are various formulations and dispensing methods for compositions of this invention. The appropriate dosages may be determined as discussed above within the bounds of this invention regarding initial and subsequent doses with regard to the relative amounts of the amoxicillin and clavulanate potassium. Delivery methods include but are not limited to liquid and oral suspensions. Dispensing systems include containers, syringes, spoons, straws and the like.

The inventive pediatric oral suspension composition containing the reduced amount of clavulanate potassium compared to conventional compositions should correspondingly reduce possible less common but severe side effects of jaundice and hepatitis, hemorrhagic/pseudomembranous colitis, angioedema, Stevens-Johnson syndrome, hypersensitivity vasculitis, tooth discoloration, and seizure, as well as the more common and disruptive side effects of diarrhea, vomiting or diaper rash, headache, mycosis, vaginitis and agitation, all while still maintaining the efficacy and benefits of the antibiotic treatment for acute otitis media and other illnesses. This should be seen whether the clavulanate potassium remains in a constant dosage throughout the about one to about fourteen day treatment regimen method, of less than about 21.5 mg/5 mL, or if the clavulanate potassium dosage is reduced through the respective about one day to about fourteen day dosage, being reduced either once, more than once or with each subsequent unit dose.

The present invention thus is a pediatric oral suspension composition having amoxicillin-clavulanate potassium of minimally sufficient quantity so as to maintain the efficacy of the composition in view of beta-lactamase mediated resistance *H. influenzae* and *M. catarrhalis*, without elevating the possibility of the severe side effects of jaundice and hepatitis and the more common and disruptive side effects of diarrhea, diaper rash and vomiting. The composition allows the amoxicillin to be used as intended while reducing the side effects of the clavulanate potassium while further still maintaining the efficacy of the overall composition when dealing with various beta-lactamase medicated resistance issues.

Further, the reduced dosage treatment of the present invention may either be maintained throughout the treatment or further reduced throughout the treatments over subsequent days. Again, this reduced amount of clavulanate potassium in the total composition may be constant throughout the treatment regimen or preferably reduced throughout the treatment regimen, with the amount being of minimal sufficient quantity so as to maintain the efficacy of the total composition in view of beta-lactamase mediated resistance *H. influenzae* and *M. catarrhalis*.

Having generally described the invention, the same will be more readily understood by reference to the following example, which is provided by way of illustration and are not intended as limiting.

EXAMPLE

Formulations:

These formulations are provided as examples of possible oral suspension formulations of this invention. It will be apparent that these formulations and many variations of these formulations are available as compositions of this invention. Other types of formulations as discussed above such as aerosols, injectable solutions, capsules, topical formulations, and others may be included among these examples.

Oral Suspension (Amounts in 5 mL)
200 mg Amoxicillin trihydrate and 3.36 mg (0.15 mEq) sodium
250 mg Amoxicillin trihydrate and 3.39 mg (0.15 mEq) sodium
400 mg Amoxicillin trihydrate and 4.33 mg (0.19 mEq) sodium
20 mg clavulanate potassium
10 mg clavulanate potassium
5 mg clavulanate potassium
Oral Suspension:
200, 250, 400 mg Amoxicillin trihydrate
20, 10, 5 mg clavulanate potassium
FD&C Red No 3
flavorings
silica gel
sodium benzoate
sodium citrate
sucrose
xanthan gum These ingredients are sieved and milled separately and together, then blended and remilled, compacted by roller compaction, and screened with vibration to provide granules.

Assays

In order to confirm the effectiveness of the compositions of this invention, various biological assays may be performed. In vitro studies of various types known for antibiotic use may be used to demonstrate effectiveness and safety. Similarly in vivo studies in animal models may also be used for such purposes. Clinical studies are not required, but clinical data may be included to show the safety and effectiveness of the compositions of this invention.

Minimum inhibitory concentrations (MICs) or minimum bactericidal concentration (MBC) for relevant bacterial populations may be determined by known quantitative methods. The MIC is the lowest concentration that inhibits visible growth on a plate or reduces turbidity in culture and provide estimates of the susceptibility of given bacteria to the compositions tested. The MBC is the lowest concentration that kills almost all (99.9%) of the original culture in a given period of time.

For the MIC, the relevant bacteria (for example *H. influenzae* or *S. pneumoniae*) may be obtained from a culture collection such as the ATCC. The bacteria can be grown on nutrient agar plates. A disk diffusion test can then be performed. Paper disks containing amoxicillin-clavulanate potassium in different dilutions representing compositions are placed on the lawn of bacteria on the plate. Inhibition zones dependent on the effectiveness of the concentrations will appear and be measured for comparison with known standard zones for amoxicillin and clavulanate potassium. Zones equal to or greater than standard zones indicate extent of effectiveness.

For the MBC, the bacteria can be grown in the appropriate nutrient broth in test tubes. An MBC may be performed by introducing dilutions of a composition into tubes with the standardized inoculum of bacteria and comparing the turbidity by eye and by standard measuring procedures to determine the concentration at which there is minimal turbidity corresponding to 99.9% inhibition.

Using these tests the effectiveness of the compositions of this invention may be demonstrated. One dilution pattern to be used would employ a constant concentration of amoxicillin combined with sequential dilutions of clavulanate potassium. The dilutions could begin at 20 mcg amoxicillin and 10 mcg clavulanate potassium per standard agar plate, and proceed by tenfold dilutions of clavulanate potassium, for example. MIC and MBC values may be measured by known methods and compared with standards, for example standards established for existing amoxicillin/clavulanate potassium combinations.

Further studies may be performed demonstrating the effectiveness of the compositions of this invention, for example MIC and bioavailability studies in mice. Such studies are well known and standardized. Different concentrations of the compositions of this invention could be administered to infected animals, in particular compositions with the same amount of amoxicillin and dilutions of clavulanate potassium, and the effectiveness determined by known methods.

The invention has been described in terms of embodiments thereof, but is more broadly applicable as will be understood by those skilled in the art. The scope of the invention is only limited by the following claims.

The invention claimed is:

1. A method of treating acute otitis media in pediatric patients under 24 months of age which patients have had frequent exposure to other children and/or have been previously treated with antibiotics, which method comprises providing two or more dosages of an oral suspension containing amoxicillin combined with clavulanate potassium in a ratio of 28:1 and administered at a daily dosage of 80-90 mg/kg of amoxicillin per pediatric patient and 2.85-3.2 mg/kg of clavulanate potassium per pediatric patient.

2. The method of claim 1 wherein the initial dosage has more clavulanate potassium than subsequent dosages.

3. The method of claim 1 wherein the dosages are given for up to fourteen days.

4. The method of claim 1 wherein the amount of amoxicillin in each dosage is from about 200 to 600 mg/5 of suspension and the amount of clavulanate potassium in the first dosage is from about 0.1 to 21.5 mg/5 mL of suspension.

5. The method of claim 1 further comprising adding a pain reduction medication to the oral suspension.

6. The method of claim 5 wherein the medication is chosen from acetaminophen, non-steroidal anti-inflammatory medication, or antipyretic medication.

7. A method of treating pediatric patients under 24 months of age for a drug resistant bacteria infection which patients have had frequent exposure to other children and/or have been previously treated with antibiotics, which method comprises providing two or more dosages of an oral suspension containing amoxicillin combined with clavulanate potassium wherein the amoxicillin is present in an amount about 200 to about 600 mg/5 mL and administered at a daily dosage of 80-90 mg/kg per pediatric patient and the clavulanate potassium is present in an amount equal to or less than about 21.5 mg/5 mL and administered at a daily dosage of 2.85-3.2 mg/kg per pediatric patient.

8. The method of claim 7 wherein the initial dosage has more clavulanate potassium than subsequent dosages.

9. The method of claim 7 wherein the dosages are given for up to fourteen days.

10. The method of claim 7 wherein the amount of clavulanate potassium in the first dosage is from about 0.1 to 21.5 mg/5 mL of suspension.

11. The method of claim 7 wherein the amount of amoxicillin in each dosage is present in an amount of about 80 mg/kg per day per pediatric patient and the clavulanate potassium is present in an amount of about 2.85 mg/kg per day per pediatric patient.

12. The method of claim 7 further comprising adding a pain reduction medication to the oral suspension.

13. The method of claim 12 wherein the medication is chosen from acetaminophen, non-steroidal anti-inflammatory medication, or antipyretic medication.

14. The method of claim 7 wherein the antimicrobial resistant bacterial infection is selected from *S. pneumoniae, H. influenzae*, and *M. catarrhalis*.

15. A method of treating beta-lactamase producing *H. influenzae* and *M. catarrhalis* in pediatric patients under 24 months of age which comprises providing two or more dosages of an oral suspension containing amoxicillin combined with clavulanate potassium wherein the amoxicillin is present in an amount about 200 to about 600 mg/5 mL and administered at a daily dosage of 80-90 mg/kg per pediatric patient and the clavulanate potassium is present in an amount equal to or less than about 21.5 mg/5 mL and administered at a daily dosage of 2.85-3.2 mg/kg per pediatric patient.

16. The method of claim 15 wherein the initial dosage has more clavulanate potassium than subsequent dosages.

17. The method of claim 15 wherein the dosages are given for up to fourteen days.

18. The method of claim 15 wherein the amount of clavulanate potassium in the first dosage is from about 0.1 to 21.5 mg/5 mL of suspension.

19. The method of claim 15 further comprising adding a pain reduction medication to the oral suspension.

20. The method of claim 19 wherein the medication is chosen from acetaminophen, non-steroidal anti-inflammatory medication, or antipyretic medication.

21. The method of claim 1 wherein the amoxicillin is present in an amount of about 80 mg/kg per day per pediatric patient and the clavulanate potassium is present in an amount of about 2.85 mg/kg per day per pediatric patient.

22. The method of claim 1 wherein the amoxicillin is present in an amount of about 40 mg/kg per dose per pediatric patient and the clavulanate potassium is present in an amount of about 1.425 mg/kg per dose per pediatric patient.

* * * * *